US00PP16452P2

(12) United States Plant Patent
Kolster

(10) Patent No.: US PP16,452 P2
(45) Date of Patent: Apr. 18, 2006

(54) ***WEIGELA* PLANT NAMED 'KOLMAS'**

(50) Latin Name: *Weigela florida*
Varietal Denomination: Kolmas

(75) Inventor: Peter Rudolf Kolster, Boskoop (NL)

(73) Assignee: Gebr. Kolster B.V., Boskoop (NL)

( * ) Notice: Subject to any disclaimer, the term of this patent is extended or adjusted under 35 U.S.C. 154(b) by 39 days.

(21) Appl. No.: 10/878,426

(22) Filed: Jun. 28, 2004

(51) Int. Cl.
*A01H 5/00* (2006.01)

(52) U.S. Cl. ..... Plt./226
(58) Field of Classification Search ..... Plt./226
See application file for complete search history.

(56) References Cited

PUBLICATIONS

The New Royal Horticultural Society Dictionary of Gardening, 1992. 4, R to Z, pp. 702 and 704.*

* cited by examiner

* cited by examiner

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Weigela* plant named 'Kolmas', characterized by its upright and outwardly spreading plant habit; dark reddish brown young stem coloration; and large green and pale yellow to white variegated leaves.

2 Drawing Sheets

Botanical classification/cultivar designation: *Weigela florida* cultivar Kolmas.

BACKGROUND OF THE INVENTION

The present Invention relates to a new and distinct cultivar of *Weigela* plant, botanically known as *Weigela florida*, and hereinafter referred to by the name 'Kolmas'.

The new *Weigela* is a product of a planned breeding program conducted by the Inventor in Boskoop, The Netherlands. The objective of the breeding program was to develop new *Weigela* cultivars with variegated leaves.

The new cultivar originated from a cross-pollination made by the Inventor in 1998 of two unidentified proprietary seedling selections, not patented. The cultivar Kolmas was discovered and selected by the Inventor in 1999 as a single flowering plant within the progeny of the stated cross-pollination in a controlled environment in Boskoop, The Netherlands.

Asexual reproduction of the new *Weigela* by terminal cuttings at Boskoop, The Netherlands since 1999, has shown that the unique features of this new *Weigela* are stable and reproduced true to type in successive generations of asexual reproduction.

SUMMARY OF THE INVENTION

The following traits have been repeatedly observed and are determined to be the unique characteristics of 'Kolmas'. These characteristics in combination distinguish 'Kolmas' as a new and distinct cultivar:

1. Upright and outwardly spreading plant habit.
2. Dark reddish brown young stem coloration.
3. Large green and pale yellow to white variegated leaves.

Plants of the new *Weigela* differ primarily from plants of the parent selections in leaf variegation coloration.

Plants of the new *Weigela* can be compared to plants of the *Weigela* cultivar Nana Variegata, not patented. However, plants of the new *Weigela* differ from plants of 'Nana Variegata' in leaf coloration as leaves of plants of 'Nana Variegata' are green and white in color. In addition, plans of the new *Weigela* have larger leaves than plants of the cultivar Nana Variegata.

BRIEF DESCRIPTION OF THE PHOTOGRAPHS

The accompanying colored photographs illustrate the overall appearance of the new *Weigela*, showing the colors as true as it is reasonably possible to obtain in colored reproductions of this type. Colors in the photographs may differ slightly from the color values cited in the detailed botanical description which accurately describe the colors of the new *Weigela*.

The photograph on the first sheet comprises a side perspective view of typical plants of 'Kolmas'.

The photograph at the top of the second sheet is a close-up view of typical flowers and leaves of 'Kolmas'.

The photograph at the bottom of the second sheet is a close-up view of typical upper surfaces of fully expanded leaves of 'Kolmas'.

DETAILED BOTANICAL DESCRIPTION

The new *Weigela* has not been observed under all possible environmental conditions. The phenotype may vary somewhat with variations in environment such as temperature and light intensity, without, however, any variance in genotype.

The aforementioned photographs, following observations and measurements describe plants grown in Boskoop, The Netherlands, in an outdoor nursery and under commercial production practices. Plants were about two years old and pruned annually. The photographs and description were taken during the summer when day temperatures ranged from 14 to 30° C. and night temperatures ranged from 5 to 11° C.

In the following descriptions, color references are made to The Royal Horticultural Society Colour Chart, 2001 Edition, except where general terms of ordinary dictionary significance are used.

Botanical classification: *Weigela florida* cultivar Kolmas.

Parentage:

*Female parent.*—Unidentified proprietary selection of *Weigela florida*, not patented.

*Male parent.*—Unidentified proprietary selection of *Weigela florida*, not patented.

Propagation:

*Type.*—Terminal cuttings.

*Time to initiate roots.*—Summer: About 30 days at 20° C. Winter: About 40 days at 12° C.

*Time to produce a rooted young plant.*—About three months at 20° C.

*Root description.*—Moderately branching; medium thickness; soft brown in color.

Plant description:

*Plant form.*—Upright and outwardly spreading perennial shrub; broad.

*Growth habit.*—Vigorous; dense and bushy growth habit.

*Plant height.*—About 1.25 meters.

*Plant width (spread).*—About 1.5 meters.

*Growth rate.*—Plants grow about 25 cm per month during the spring in Boskoop, The Netherlands.

*Lateral branches.*—Quantity per plant: About eight. Length: About 40 cm. Diameter: About 3.5 mm. Internode length: About 7.1 cm. Strength: Strong. Texture: Smooth, Glabrous. Color: 178A; shaded, 143C to 144B. Lenticels: Density: Sparse. Length: About 1 mm. Width: About 0.2 mm. Color: Close to 192D.

*Foliage description.*—Leaves opposite, single, and generally symmetrical. Length: About 12.6 cm. Width: About 6.6 cm. Shape: Ovate to elliptic. Apex: Aristate. Base: Attenuate. Margin: Finely serrulate. Texture, upper and lower surfaces: Slightly rugose; pubescent. Venation pattern: Pinnate. Color: Developing leaves, upper surface: Center, Slightly more yellow than 137A; towards the margins 1D; towards apex, occasionally tinted with 180A. Developing leaves, lower surface: Center, 138A to 138B; towards the margins 1D; towards apex, occasionally tinted with 180A. Fully expanded leaves, upper surface: Center, more green than 147A; towards the margins between 155A and 157A; towards apex, occasionally tinted with 180A. Fully expanded leaves, lower surface: Center, 138B; towards the margins 155A; towards apex, occasionally tinted with 180A. Venation, upper surface: 146C. Venation, lower surface: 144C; towards base, 151A. Petiole: Length: About 8 mm. Diameter: About 3 mm. Color, upper and lower surfaces: 151A.

Flower description:

*FLower type and habit.*—Pink single campanulate flowers arranged in terminal and axillary pairs or small clusters of three flowers; about 58 flowers and flower buds per lateral branch. Flowers not persistent. Flowers face mostly upright or slightly outward.

*Natural flowering season.*—Plants flower twice a year. First flowering period is in the spring, typically May in Boskoop, The Netherlands; the second flowering period is late summer, typically August to September in Boskoop, The Netherlands; flowering periods last about one month; flowering continuous during these periods.

*Postproduction longevity.*—Flowers typically last about five days on the plant.

*Fragrance.*—None detected.

*Flower buds.*—Height: About 2.2 cm. Diameter: About 6 mm. Shape: Oblanceolate. Color: 59D to 182A.

*Flowers.*—Diameter: About 2.3 cm. Depth: About 3.4 cm. Throat diameter: About 5 mm.

*Petals.*—Quantity per flower: Five, fused at base. Lobe length: About 1.5 cm. Width: About 9 mm. Shape: Oblanceolate. Aspect: Apices, slightly reflexed. Apex: Obtuse. Margin: Entire. Texture, upper and lower surfaces: Smooth, glabrous. Color: When opening and fully opened, upper surface: 69B to 69C to pure white, close to 155D. Color becoming closer to 70C with development. When opening and fully opened, lower surface: 64D; towards the margins and apex, 69D to close to 155D. Throat and tube: Close to 64D.

*Sepals.*—Quantity per flower: Five, fused at base. Length: About 9 mm. Width: About 1 mm. Shape: Linear. Apex: Acute. Margin: Entire. Texture, upper and lower surfaces: Mostly glabrous; margins, pubescent. Color, upper surface: 143A to 143B. Color, lower surface: 144A to 144B.

*Peduncles.*—Length: About 1.2 cm. Diameter: About 1 mm. Orientation: About 5 to 25° from vertical. Strength: Moderately strong. Color: 143B.

*Reproductive organs.*—Stamens: Quantity per flower. About five. Anther shape: Narrowly oblong. Anther length: About 2 mm. Anther color: 155A. Filament length: About 2.5 mm. Filament color: 144A. Pollen amount: None. Pistils: Quantity per flower: One. Pistil length: About 3.1 mm. Stigma shape: Globular, flattened. Stigma color: 155A. Style length: About 3 mm. Style color: 155A; towards the apex, 69C to 69D; towards the base, 145C to 145D. Ovary color: 143C.

*Seed/fruit.*—Seed and fruit development have not been observed.

Disease/pest resistance: Plants of the new *Weigela* have not been observed to be resistant to pathogens and pests common to *Weigela*.

Temperature tolerance: Plants of the new *Weigela* have been observed to tolerate temperatures ranging from −20 to 35° C.

It is claimed:

1. A new and distinct cultivar of *Weigela* plant named 'Kolmas', as illustrated and described.

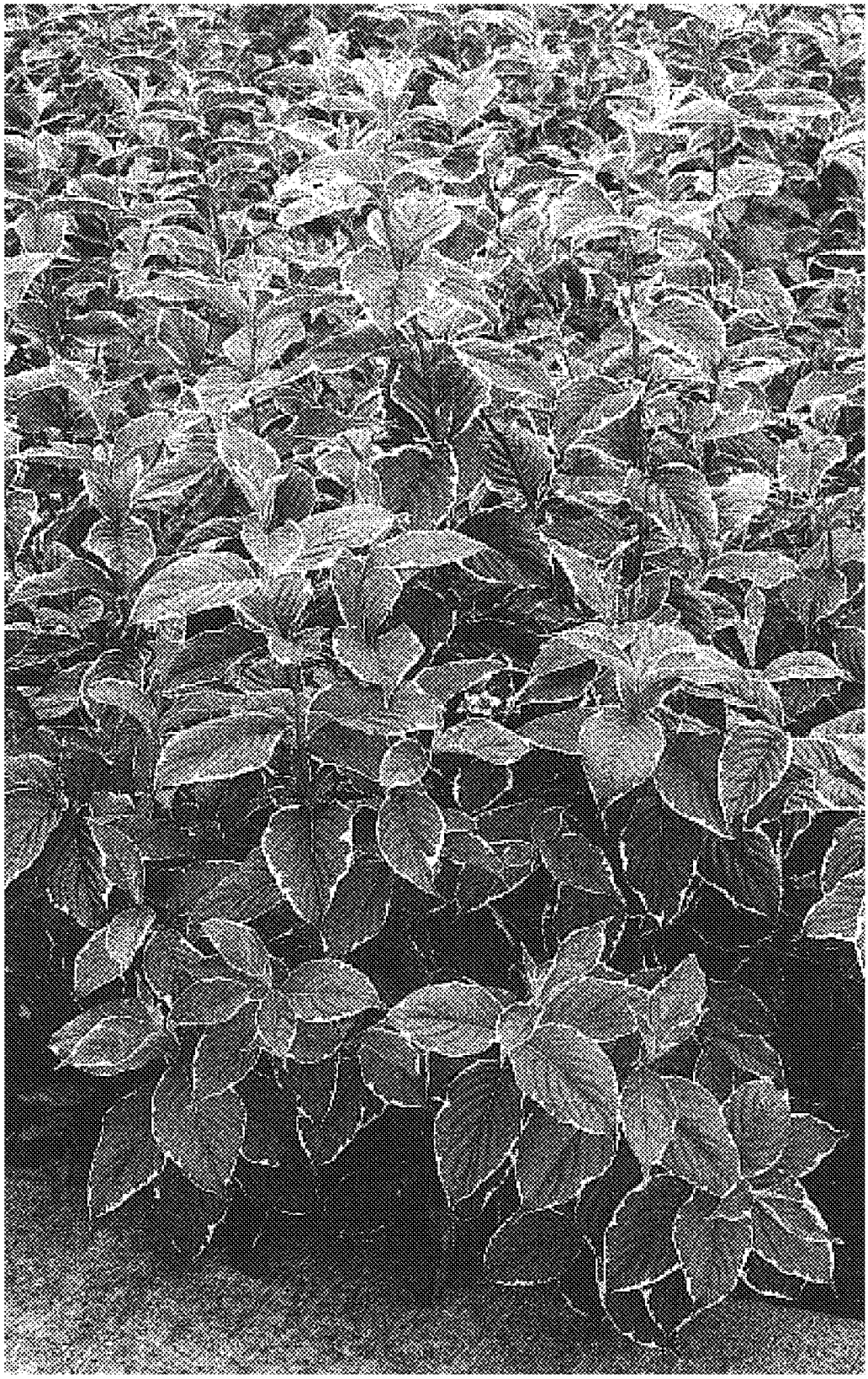

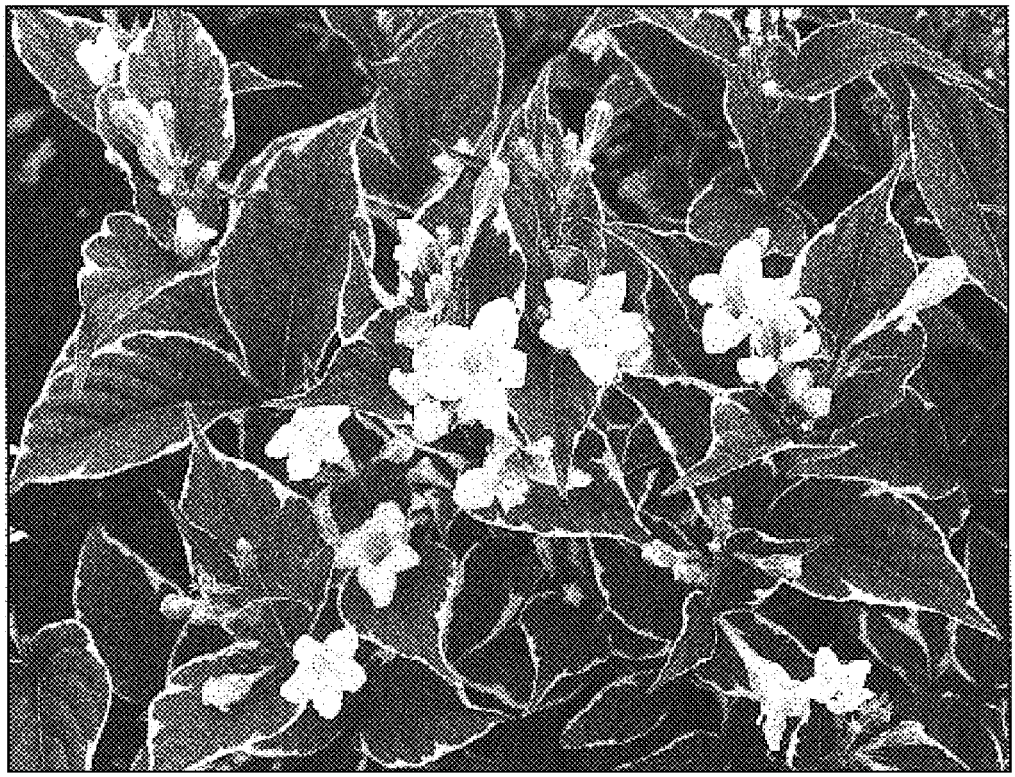
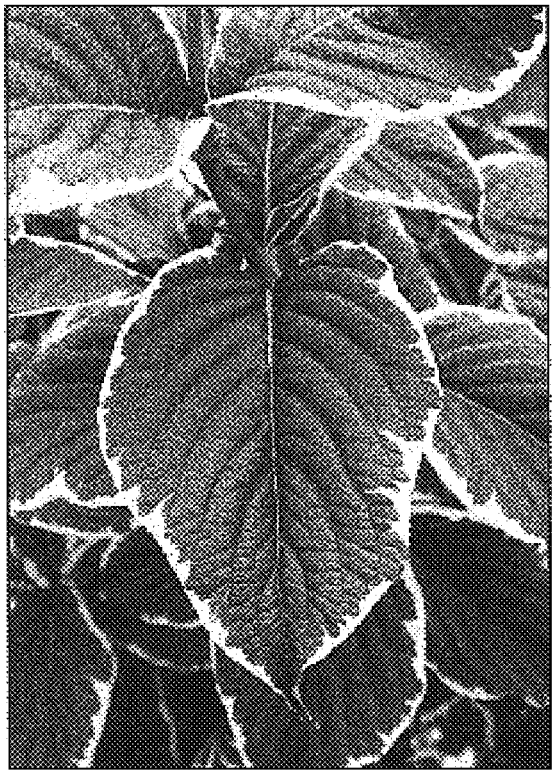

* * * * *